United States Patent
Dutta et al.

(10) Patent No.: US 10,287,400 B2
(45) Date of Patent: May 14, 2019

(54) CURABLE SILICONE COMPOSITION AND APPLICATIONS AND USES THEREOF

(71) Applicant: Momentive Performance Materials Inc., Waterford, NY (US)

(72) Inventors: Pranabesh Dutta, Bangalore (IN); Shashikala Indudhara Swamy, Bangalore (IN); Amol Murlidharrao Kendhale, Bangalore (IN); Manav Gupta, Bangalore (IN); Anantharaman Dhanabalan, Bangalore (IN)

(73) Assignee: Momentive Performance Materials Inc., Waterford, NY (US)

( * ) Notice: Subject to any disclaimer, the term of this patent is extended or adjusted under 35 U.S.C. 154(b) by 75 days.

(21) Appl. No.: 15/098,534

(22) Filed: Apr. 14, 2016

(65) Prior Publication Data
US 2017/0298188 A1 Oct. 19, 2017

(51) Int. Cl.
| | |
|---|---|
| C08G 77/00 | (2006.01) |
| A61K 8/89 | (2006.01) |
| A61Q 5/02 | (2006.01) |
| A61Q 5/12 | (2006.01) |
| A61Q 17/04 | (2006.01) |
| C08K 5/56 | (2006.01) |
| C08G 77/50 | (2006.01) |
| C08L 83/00 | (2006.01) |
| C08L 83/14 | (2006.01) |
| A61K 8/891 | (2006.01) |

(52) U.S. Cl.
CPC ............... *C08G 77/80* (2013.01); *A61K 8/89* (2013.01); *A61K 8/891* (2013.01); *A61Q 5/02* (2013.01); *A61Q 5/12* (2013.01); *A61Q 17/04* (2013.01); *C08G 77/50* (2013.01); *C08K 5/56* (2013.01); *C08L 83/00* (2013.01); *C08L 83/14* (2013.01); *A61K 2800/81* (2013.01)

(58) Field of Classification Search
CPC ......... C08G 77/50; C08G 77/12; C08G 77/20
See application file for complete search history.

(56) References Cited

U.S. PATENT DOCUMENTS

| | | | |
|---|---|---|---|
| 6,844,409 B2 | 1/2005 | Angeletakis et al. | |
| 6,911,518 B2 | 6/2005 | Lichtenhan et al. | |
| 7,323,250 B2 | 1/2008 | Tabei et al. | |
| 7,700,697 B2 | 4/2010 | Tabei | |
| 7,714,053 B2 | 5/2010 | Adler et al. | |
| 8,200,058 B2 | 6/2012 | Choki et al. | |
| 8,420,293 B2 | 4/2013 | Choki et al. | |
| 8,431,625 B2 | 4/2013 | Luchterhandt et al. | |
| 8,608,846 B2 | 12/2013 | Mizushima et al. | |
| 2005/0080154 A1* | 4/2005 | Tabei .................. C08L 83/04 522/148 |
| 2011/0054106 A1 | 3/2011 | Sano | |
| 2012/0220722 A1 | 8/2012 | Shiobara et al. | |

FOREIGN PATENT DOCUMENTS

| | | | |
|---|---|---|---|
| EP | 927736 | * | 7/1999 |
| GB | 1458174 A | | 12/1976 |
| JP | 62207333 A | | 9/1987 |
| JP | 2011012113 A | | 1/2011 |
| JP | 2012046604 A | | 3/2012 |
| JP | 2015229681 A | | 12/2015 |
| WO | 1999007713 A1 | | 2/1999 |
| WO | 200036665 A1 | | 6/2000 |
| WO | 200181649 A1 | | 11/2001 |
| WO | 2003094256 A2 | | 11/2003 |
| WO | 2004089620 A2 | | 10/2004 |
| WO | 2008057045 A1 | | 5/2008 |

OTHER PUBLICATIONS

Patent Cooperation Treaty (PCT), International Search Report and Written Opinion for Application PCT/US2017/024897 filed Mar. 30, 2017, dated Jun. 20, 2017, International Searching Authority, EP.

* cited by examiner

*Primary Examiner* — Kuo Liang Peng
(74) *Attorney, Agent, or Firm* — Joseph Waters; McDonald Hopkins LLC

(57) ABSTRACT

A curable composition comprising (a) an organopolysiloxane comprising a curable functional group; (b) a cross-linker comprising a silyl hydride group or a thiol group; (c) a reaction accelerator; (d) optionally an inhibitor; and (e) optionally other additives. The curable composition exhibits high refractive index and optical clarity. The curable composition can be used to prepare a cured material that exhibits high refractive index, optical clarity, crack resistance, and low moisture vapor permeability.

30 Claims, No Drawings

CURABLE SILICONE COMPOSITION AND APPLICATIONS AND USES THEREOF

FIELD OF INVENTION

The present invention relates to a curable silicone composition. In particular, the present invention relates to curable silicone composition comprising an organopolysiloxane. The curable silicone compositions may be used to form cured materials that may exhibit one or more of high refractive index, good moisture vapor permeability, high thermal resistance, crack resistance, and optical clarity. The curable composition may be used in a variety of applications including as a sealant, an encapsulant, a barrier coating layer, etc., and may find application in various environments including in electronic devices.

BACKGROUND

Many of the next generation flexible printed electronic displays such as organic light emitting diodes (OLEDs), organic photovoltaic displays (OPVs), organic thin film transistors (OTFTs), etc., are extremely sensitive to atmospheric moisture vapor and oxygen, which limits the lifetime of the display devices and their widespread commercialization.

The current encapsulation technology generally available in the field or moisture sensitive organic electronic devices is a glass lid with a getter material fixed to the substrate by epoxy glue. The getter materials, such as, e.g., calcium oxide or barium oxide, are incorporated into the package to react with any byproducts of the resin cure process or any residual water incorporated in the package or diffusing through the epoxy seal over time. Although the glass has been used prevalently as an encapsulant or barrier layer due to its low permeability to water vapor and oxygen transmission, the main drawback with glass encapsulated technology is that the resultant devices become non-flexible and rigid, which cannot satisfy the applications demanding flexible devices.

Several attempts have been made to develop flexible barrier films. These include multilayer systems of alternating inorganic and organic layers (often more than 10 layers). Such systems are described in, for example, WO 00/36665 A1, WO01/81649 A1, WO 2004/089620 A2, WO 03/094256 A2, and WO2008/057045 A1. Although, the multilayer thin film technology provides good barrier properties and serves the purpose of encapsulation to the electronic devices, the complex nature and high cost of thin film preparation do not make them feasible in large area and large scale manufacturing processes. It is therefore desirable to provide substrates with improved barrier properties that can protect the display devices from the premature deterioration and extend their lifetimes.

SUMMARY

The following presents a summary of this disclosure to provide a basic understanding of some aspects. This summary is intended to neither identify key or critical elements nor define any limitations of embodiments or claims. Furthermore, this summary may provide a simplified overview of some aspects that may be described in greater detail in other portions of this disclosure.

In accordance with various aspects and embodiments, the present technology provides a curable silicone composition comprising an organopolysiloxane. The organopolysiloxane comprises organofunctional groups in the main chain of the polysiloxane. Cured materials formed from compositions comprising such organopolysiloxanes have been found to exhibit relatively high refractive index, good optical clarity (e.g., low yellowing), flexibility, thermal resistivity, crack resistivity, and/or moisture permeability.

In various aspects, the present invention provides a curable composition suitable for thin film flexible encapsulation technology, which not only reduce the overall complexity but also provide high quality barrier films that are scalable and easy processable for making large area display devices.

The present invention provides, in aspects and embodiments thereof, a low moisture permeable siloxane composition, which can provide a cured material with high refractive index and/or improved barrier properties suitable for use in an organic electroluminescent display device and prolong their lifetime. In one aspect, this invention provides a curable composition of bicyclic modified silicone containing compounds wherein the bicyclic compound can be present in a terminal position, as a pendant group, and/or in the backbone of the silicone polymers. Methods of making the bicyclic modified silicone-containing compound, and methods of making cured materials from compositions are disclosed.

In one aspect, the present invention provides, a curable silicone composition comprising:

(A) an organopolysiloxane with a formula:

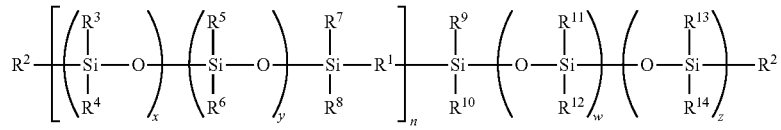

where $R^1$ is a divalent organic group chosen from a C1-C20 divalent hydrocarbon, a C4-C20 branched divalent hydrocarbon, or a C4-C30 cyclic-containing hydrocarbon group;

$R^2$ is a curable functional group independently chosen from
  a vinyl, a vinyl-containing group, an unsaturated hydrocarbon, an unsaturated cyclic hydrocarbon, an acrylate, a methacrylate, a hydroxy, an alkoxy, and an epoxy;

$R^3$-$R^{14}$ are independently chosen from hydrogen, a C1-C10 monovalent hydrocarbon group, a C6-C20 monovalent aromatic group, and a C4 to C30 monovalent saturated or unsaturated cycloalkyl group;

x and z are independently 1-30;

y and w are independently 0-30; and n is 1-30;

(B) a cross-linker selected from a compound comprising at least one —SiH group, at least one —SH group, or a combination of two or more thereof;

(C) a reaction accelerating agent selected from a photoinitiator, a thermal initiator, a metal containing catalyst, or a combination of two or more thereof;

(D) optionally an inhibitor; and (E) optionally one or more additives.

In one embodiment of the curable silicone composition, $R^1$ is chosen from a divalent group comprising a C4-C30 cyclic-containing hydrocarbon group chosen from a cyclobutyl group, cyclopentyl group, a cyclohexyl group, a cycloheptyl group, a cyclooctyl group, 1,1-diethenyl cylcohexane; 1,3-diethenyl cylcohexane; bicyclo[2.2.1]-2,5-dienthenylheptane; 1,4-di-2-prope-1-nylcyclochexane; 1,3-diisopropenylbenzene; a spiro[5.5]-3,8-diethenylundecane; a 1,3-diethenyladamantane; a vinyl norbornene; 3,9-divinyl-2,4,8,10-tetraoxaspiro[5.5]undecane; pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5]undecane, bicyclo[1.1.0]butane, bicyclo[2.1.0]pentane, bicyclo[2.2.0]hexane, bicyclo[3.1.0]hexane, bicyclo[3.2.0]heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.2.2]nonane, bicyclo[3.3.1]nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings.

In one embodiment of the curable silicone composition of any previous embodiment, $R^2$ is chosen from a C1-C20 hydrocarbon radical comprising a vinyl functional group, a monovalent C4-C20 branched hydrocarbon radical comprising a vinyl functional group, or a monovalent C4 to C30 cyclic hydrocarbon radical comprising a vinyl functional group.

In one embodiment of the curable silicone composition of any previous embodiment, $R^2$ is of the formula X—$R^{16}$— where X is the curable functional group chosen from a vinyl group ($CH_2=CH_2$—), an unsaturated cyclic group, an unsaturated polycyclic group, and $R^{16}$ is a bond or a monovalent hydrocarbon. In one embodiment, X is chosen from cyclopentene, cyclohexene, cyclooctene, pinene, bornene, norpinene, norbornene, spiro[2.2]pentene, spiro[2.3]hexene, spiro[2.4]heptene, spiro[2.5]octene, spiro[3.3]heptene, spiro[3.4]octene, spiro[3.5]nonene, spiro[4.4]nonene, spiro[4.5]decene, spiro[5.5]undecene, bicyclo[1.1.0]butene, bicyclo[2.1.0]pentene, bicyclo[2.2.0]hexene, bicyclo[3.1.0]hexene, bicyclo[3.2.0]heptene, bicyclo[3.3.0]octene, bicyclo[4.1.0]heptene, bicyclo[4.2.0]octene, bicyclo[4.3.0]nonene, bicyclo[4.4.0]decene, bicyclo[1.1.1]pentene, bicyclo[2.1.1]hexene, bicyclo[2.2.1]heptene, bicyclo[2.2.2]octene, bicyclo[3.1.1]heptene, bicyclo[3.2.1]octene, bicyclo[3.2.2]nonene, bicyclo[3.3.1]nonene, bicyclo[3.3.2]decene, bicyclo[3.3.3]undecene, an adamantene, tricyclo[5.2.1.0$^{2,6}$]decene, tricyclo[4.3.1.1$^{2,5}$]undecene rings, a limonene, a camphene, a limonene oxide, a vinyl cyclohexyl epoxide, a dicyclopentadiene, 5-ethylidene-2-norbornene, 2-vinyl adamantane, 2-methylene adamantane, or (−)-beta-chamigrene, 4-vinyl cyclohexyl.

In one embodiment of the curable silicone composition of any previous embodiment, the cross-linker (B) is chosen from a silicone-containing compound comprising at least one —SiH group, at least one —SH group, or a combination of two or more thereof. In one embodiment, the silicone-containing compound is chosen from a cyclic silicone, a linear silicone, a branched silicone, or a combination of two or more thereof.

In one embodiment of the curable silicone composition of any previous embodiment, the cross-linker (B) is of the formula:

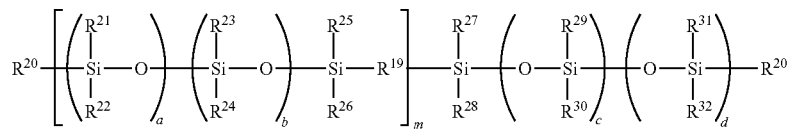

where $R^{19}$ is a divalent organic group chosen from a C1-C20 divalent hydrocarbon, a C4-C20 branched divalent hydrocarbon, or a C4-C30 cyclic-containing divalent hydrocarbon group;

$R^{20}$ is a functional group chosen from hydrogen, an acrylate, a methacrylate, a thiol, or $R^2$;

$R^{21}$-$R^{32}$ are independently chosen from hydrogen, a C1-C10 monovalent hydrocarbon group, a $C^6$-$C^{20}$ monovalent aromatic group, and a C4 to C30 monovalent cycloalkyl group;

a and d are independently 1-30;

b and c are independently 0-30; and m is 1-30.

In one embodiment, $R^{19}$ is chosen from a divalent organic group comprising a C4-C30 cyclic-containing hydrocarbon group chosen from a cyclopentyl group, a cyclohexyl group, a cycloheptyl group, cyclooctyl group, bicyclo[2.2.1]hepta-2,5-diene; a 1,1-diethenyl cylcohexane; a 1,3-diethenyl cylcohexane; a bicyclo[2.2.1]-2,5-dienthenylheptane; a 1,4-di-2-prope-1-nylcyclochexane; a 1,3-diisopropenylbenzene; a spiro[5.5]-3,8-diethenylundecane; a 1,3-diethenyladamantane; a vinyl norbornene; 3,9-divinyl-2,4,8,10-tetraoxaspiro[5.5]undecane; pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5]undecane, bicyclo[1.1.0]butane, bicyclo[2.1.0]pentane, bicyclo[2.2.0]hexane, bicyclo[3.1.0]hexane, bicyclo[3.2.0]heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.2.2]nonane, bicyclo[3.3.1]nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings.

In one embodiment of the curable silicone composition of any previous embodiment, the reaction accelerating agent is selected from a metal-containing catalyst.

In one embodiment of the curable silicone composition of any previous embodiment, the inhibitor is selected from an ethylenic compound, an acetylenic compound, or a combination thereof.

In one embodiment of the curable silicone composition of any previous embodiment, the additive is selected from an antioxidant, a thermal stabilizer, an adhesion promoter, a filler, or a combination of two or more thereof.

In one embodiment of the curable silicone composition of any previous embodiment, the composition has a refractive index of from 1.45 to 1.51.

In one embodiment of the curable silicone composition of any previous embodiment, the composition has a transparency of ≥95%.

In one embodiment of the curable silicone composition of any previous embodiment, the composition has a MVTR, WVTR, O permeability of $10^{-1}$ to 10 g/m²·day.

In one aspect, the present invention provides a cured article formed from the curable composition of any previous embodiment.

In one aspect, the present invention provides a cured article formed from a curable silicone composition, said curable silicone composition comprising:

(A) an organopolysiloxane with a formula:

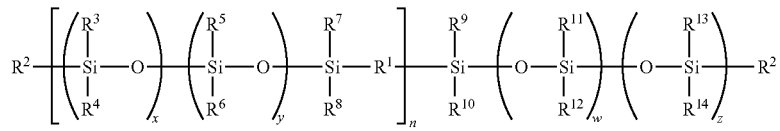

where $R^1$ is a divalent organic group chosen from a C1-C20 divalent hydrocarbon, a C4-C20 branched divalent hydrocarbon, or a C4-C30 cyclic-containing hydrocarbon group;

$R^2$ is a curable functional group independently chosen from a vinyl, a vinyl-containing group, an unsaturated hydrocarbon, an unsaturated cyclic hydrocarbon, an acrylate, a methacrylate, a hydroxy, an alkoxy, and an epoxy;

$R^3$-$R^{14}$ are independently chosen from hydrogen, a C1-C10 monovalent hydrocarbon group, a C6-C20 monovalent aromatic group, and a C4 to C30 monovalent saturated or unsaturated cycloalkyl group;

x and z are independently 1-30;

y and w are independently 0-30; and n is 1-30;

(B) a cross-linker selected from a compound comprising at least one —SiH group, at least one —SH group, or a combination of two or more thereof;

(C) a reaction accelerating agent selected from a photoinitiator, a thermal initiator, a metal containing catalyst, or a combination of two or more thereof;

(D) optionally an inhibitor; and (E) optionally one or more additives.

In one embodiment, $R^1$ is chosen from a divalent organic group comprising a C4-C30 cyclic-containing hydrocarbon group chosen from a cyclobutyl group, cyclopentyl group, a cyclohexyl group, a cycloheptyl group, cyclooctyl group, 1,1-diethenyl cylcohexane; 1,3-diethenyl cylcohexane; bicyclo[2.2.1]-2,5-dienthenylheptane; 1,4-di-2-prope-1-nyl-cyclochexane; 1,3-diisopropenylbenzene; spiro[5.5]-3,8-diethenylundecane; a1,3-diethenyladamantane; a vinyl norbornene; 3,9-divinyl-2,4,8,10-tetraoxaspiro[5.5]undecane; pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5]undecane, bicyclo[1.1.0]butane, bicyclo[2.1.0]pentane, bicyclo[2.2.0]hexane, bicyclo[3.1.0]hexane, bicyclo[3.2.0]heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.2.2]nonane, bicyclo[3.3.1]nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings.

In one embodiment of the cured article of any previous embodiment, the $R^2$ functional group chosen from a C1-C20 hydrocarbon radical comprising a vinyl functional group, a monovalent C4-C20 branched hydrocarbon radical comprising a vinyl functional group, or a monovalent C4 to C30 cyclic hydrocarbon radical comprising a vinyl functional group.

In one embodiment of the cured article of any previous embodiment, the $R^2$ group is of the formula X—$R^{16}$— where X is the curable functional group, and $R^{16}$ is a bond or a monovalent hydrocarbon radical. In embodiments, $R^{16}$ may be a C1-C20 alkylene group; a C1-C10 alkylene group; even a C1-C6 alkylene group, and X may be chosen from a vinyl group ($CH_2$=$CH_2$—), an unsaturated cyclic group, an unsaturated polycyclic group.

In one embodiment, X is chosen from cyclopentene, cyclohexene, cyclooctene, pinene, bornene, norpinene, norbornene, spiro[2.2]pentene, spiro[2.3]hexene, spiro[2.4]heptene, spiro[2.5]octene, spiro[3.3]heptene, spiro[3.4]octene, spiro[3.5]nonene, spiro[4.4]nonene, spiro[4.5]decene, spiro[5.5]undecene, bicyclo[1.1.0]butene, bicyclo[2.1.0]pentene, bicyclo[2.2.0]hexene, bicyclo[3.1.0]hexene, bicyclo[3.2.0]heptene, bicyclo[3.3.0]octene, bicyclo[4.1.0]heptene, bicyclo[4.2.0]octene, bicyclo[4.3.0]nonene, bicyclo[4.4.0]decene, bicyclo[1.1.1]pentene, bicyclo[2.1.1]hexene, bicyclo[2.2.1]heptene, bicyclo[2.2.2]octene, bicyclo[3.1.1]heptene, bicyclo[3.2.1]octene, bicyclo[3.2.2]nonene, bicyclo[3.3.1]nonene, bicyclo[3.3.2]decene, bicyclo[3.3.3]undecene, an adamantene, tricyclo[5.2.1.0$^{2,6}$]decene, tricyclo[4.3.1.1$^{2,5}$]undecene rings, a limonene, a camphene, a limonene oxide, a vinyl cyclohexyl epoxide, a dicyclopentadiene, 5-ethylidene-2-norbornene, 2-vinyl adamantane, 2-methylene adamantane, or (−)-beta-chamigrene, 4-vinyl cyclohexyl.

In one embodiment of the cured article of any previous embodiment, the cross-linker (B) is chosen from a silicone-containing compound comprising at least one —SiH group, at least on —SH group, or a combination of two or more thereof.

In one embodiment, the silicone-containing compound is chosen from a cyclic silicone, a linear silicone, a branched silicone, or a combination of two or more thereof.

In one embodiment, the linear silicone cross-linker is of general formula:

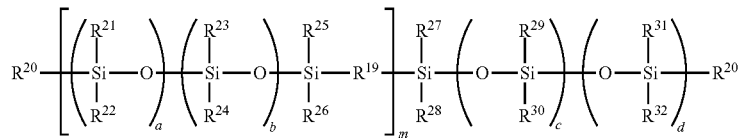

where $R^{19}$ is a divalent organic group chosen from a C1-C20 divalent hydrocarbon, a C4-C20 branched divalent hydrocarbon, or a C4-C30 cyclic-containing divalent hydrocarbon group;

$R^{20}$ is a functional group chosen from hydrogen, an acrylate, a methacrylate, a thiol, or $R^2$;

$R^{21}$-$R^{32}$ are independently chosen from hydrogen, a C1-C10 monovalent hydrocarbon group, a $C^6$-$C^{20}$ monovalent aromatic group, and a C4 to C30 monovalent cycloalkyl group;

a and d are independently 1-30;

b and c are independently 0-30; and m is 1-30.

In one embodiment, $R^{19}$ is chosen from a divalent organic group comprising a C4-C30 cyclic-containing group chosen from a cyclopentyl group, a cyclohexyl group, a cycloheptyl group, cyclooctyl group, 1,1-diethenyl cylcohexane; a 1,3-diethenyl cylcohexane; bicyclo[2.2.1]-2,5-dienthenylheptane; 1,4-di-2-prope-1-nylcyclochexane; 1,3-diisopropenyl-benzene; spiro[5.5]-3,8-diethenylundecane; 1,3-diethenyladamantane; 3,9-divinyl-2,4,8,10-tetraoxaspiro [5.5]undecane; pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5] undecane, bicyclo[1.1.0]butane, bicyclo[2.1.0]pentane, bicyclo[2.2.0]hexane, bicyclo[3.1.0]hexane, bicyclo[3.2.0] heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo [2.2.1]heptane, bicyclo[2.2.2]octane, bicyclo[3.1.1]heptane, bicyclo[3.2.1]octane, bicyclo[3.2.2]nonane, bicyclo[3.3.1] nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings.

In one embodiment of the cured article of any previous embodiment, the reaction accelerating agent is selected from a metal containing catalyst.

In one embodiment of the cured article of any previous embodiment, the inhibitor is selected from a ethylenic compounds or a acetylenic compounds or a combination thereof.

In one embodiment of the cured article of any previous embodiment, the additive is selected from an antioxidant, a thermal stabilizer, an adhesion promoter, filler, or a combination thereof.

In one embodiment of the cured article of any previous embodiment, the article has a refractive index of from 1.45 to 1.51.

In one embodiment of the cured article of any previous embodiment, the article has a transparency of ≥95%.

In one embodiment of the cured article of any previous embodiment, the article has a MVTR, WVTR, O permeability of $10^{-1}$ to 10 g/m$^2$·day.

In one embodiment of the cured article of any previous embodiment, the article is chosen from an LED encapsulant, an optical waveguide, an optical lens, an optical bonding material, an optical adhesive, an a optical film or sheet, laminated film of sheet, in electronic component or in combination with semiconductor device.

In still another aspect, the present invention provides a personal care composition comprising the curable silicone composition of any of the previous embodiments. In one embodiment, the personal care composition is chosen from a cosmetic formulation, a sunscreen, a shampoo, a conditioner, a lotion, or a cream.

DETAILED DESCRIPTION

Reference will now be made to exemplary embodiments, examples of which are illustrated in the accompanying drawings. It is to be understood that other embodiments may be utilized and structural and functional changes may be made. Moreover, features of the various embodiments may be combined or altered. As such, the following description is presented by way of illustration only and should not limit in any way the various alternatives and modifications that may be made to the illustrated embodiments. In this disclosure, numerous specific details provide a thorough understanding of the subject disclosure. It should be understood that aspects of this disclosure may be practiced with other embodiments not necessarily including all aspects described herein, etc.

As used herein, the words "example" and "exemplary" mean an instance, or illustration. The words "example" or "exemplary" do not indicate a key or preferred aspect or embodiment. The word "or" is intended to be inclusive rather than exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

The present technology provides a curable composition comprising: (a) an organopolysiloxane comprising a curable functional group; (b) a cross-linker comprising a silyl hydride group or a thiol group; (c) a reaction accelerator; (d) optionally an inhibitor; and (e) optionally other additives.

The organopolysiloxane (a) comprises a siloxane polymer having organic functional groups between silicon atoms within a part of the main chain. The organopolysiloxane (a) comprises a compound of Formula (I):

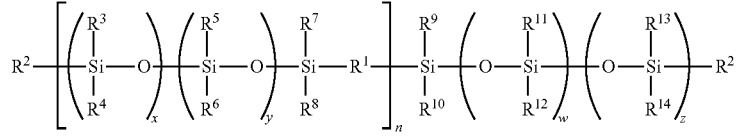

where R$^1$ is a divalent organic group chosen from a C1-C20 hydrocarbon, a C4-C20 branched hydrocarbon, or a C4-C30 cyclic-containing hydrocarbon group;

R$^2$ is a curable functional group independently chosen from a vinyl, a vinyl-containing group, an unsaturated hydrocarbon, an unsaturated cyclic hydrocarbon, an acrylate, a methacrylate, a hydroxy, an alkoxy, and an epoxy;

R$^3$-R$^{14}$ are independently chosen from hydrogen, a C1-C10 monovalent hydrocarbon group, a C6-C20 monovalent aromatic group, and a C4 to C30 monovalent saturated or unsaturated cycloalkyl group;

x and z are independently 1-30;

y and w are independently 0-30; and n is 1-30.

R$^1$ may be chosen from a divalent C1-C20 hydrocarbon or a divalent C4-C20 branched divalent hydrocarbon group. The divalent hydrocarbon group is a group formed by removing two hydrogen atoms from an alkane (either two hydrogen atoms from the same carbon or one hydrogen atom from two different carbon atoms). Examples of suitable divalent hydrocarbon groups include, but are not limited to, methylene, ethylene, propylene, butylene, pentylene, hexylene, heptylene, octylene, nonylene, isopropylene, isobutylene, etc. In embodiments, R$^1$ is chosen from a C1-C6 linear or branched alkylene.

R$^1$ may also be chosen from a divalent cyclic hydrocarbon group. As used herein a "cyclic" or "cyclic-containing" hydrocarbon group refers to a group derived by removing two hydrogen atoms from an cyclic-containing alkane, where (i) both hydrogen atoms may be removed from the same ring carbon, (ii) one hydrogen atom is removed from one ring carbon, and the other hydrogen atom is removed from another ring carbon, (iii) one hydrogen is removed from a ring carbon, and one hydrogen is removed from a hydrocarbon group attached to the chain, (iv) both hydrogen atoms are removed from the same carbon of a hydrocarbon group connected to the cyclic group, or (v) one hydrogen is removed from a first hydrocarbon group connected to the cyclic group, and one hydrogen is removed from a second hydrocarbon group connected to the cyclic group.

The cyclic group in the cyclic-containing hydrocarbon may be a monocyclic hydrocarbon group or a polycyclic hydrocarbon group. Examples of suitable monocyclic hydrocarbon groups include a cycloalkyl group having 3 to 12 carbon atoms, such as, but not limited to, cyclobutyl group, a cyclopentyl group, a cyclohexyl group, a cycloheptyl group, or a cyclooctyl group, or a cycloalkenyl group having 3 to 12 carbon atoms, such as a cyclohexenyl group. In embodiments, the monocyclic hydrocarbon group is a monocyclic hydrocarbon group having 3 to 7 carbon atoms. A cyclopentyl group and a cyclohexyl group are particularly suitable.

The polycyclic hydrocarbon groups include ring-assembly hydrocarbon groups and crosslinked-ring hydrocarbon groups. Examples of the ring-assembly hydrocarbon groups include a bicyclohexyl group, a perhydronaphthalene group, etc. Examples of crosslinked-ring hydrocarbon rings include, but are not limited to, for example, bicyclic hydrocarbon rings, tricyclic hydrocarbon rings, and tetracyclic hydrocarbon rings, such as tetracyclo[4.4.0.1$^{2,5}$.1$^{7,10}$]dodecane and perhydro-1,4-methano-5,8-methanonaphthalene rings. Further, the crosslinked-ring hydrocarbon rings include condensed-ring hydrocarbon rings, for example, condensed rings resulting from condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenarene rings.

Examples of suitable polycyclic hydrocarbon groups of 4 to 30 which may be part of or provide the R$^1$ group include, but are not limited to, pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5]undecane, bicyclo[1.1.0]butane, bicyclo[2.1.0]pentane, bicyclo[2.2.0]hexane, bicyclo[3.1.0]hexane, bicyclo[3.2.0]heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.2.2]nonane, bicyclo[3.3.1]nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings.

In embodiments, the cyclic-containing R$^1$ group may be represented by the formula: R$^{15}$-A-R$^{15}$, where R$^{15}$ is a bond or a C1-C10 monovalent hydrocarbon radical, and A is a cyclic or polycyclic hydrocarbon group. The cyclic or polycyclic group A may be a cyclic or polycyclic group as described above. It will be appreciated that the R$^{15}$ groups may be attached to the same ring carbon atom or to different carbon atoms on the ring.

Examples of suitable groups for R$^1$ include but are not limited to:

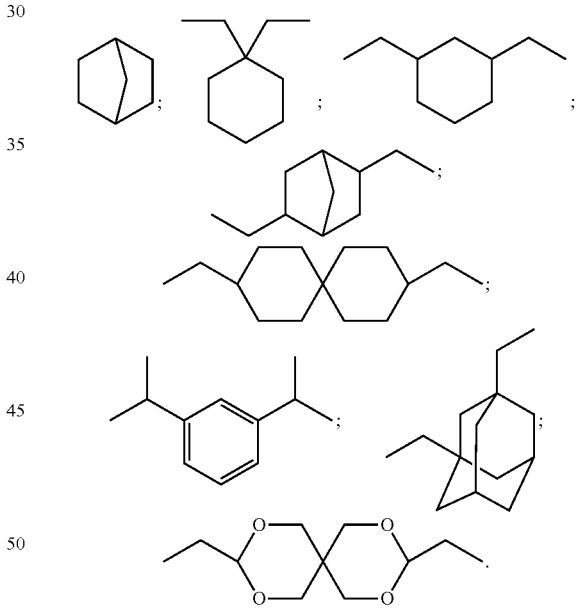

While the divalent organic groups or "alkylene" type groups for R$^1$ are described with respect to removal of a hydrogen, it will be appreciated by those of skill in the art of forming silicone-containing materials that the alkylene type groups for R$^1$ may be derived from and incorporated into the siloxane backbone by the reaction of a diene (conjugated or non-conjugated) compound comprising the desired R$^1$ group with an appropriate siloxane in the presence of a catalyst (e.g., Karstedt's catalyst).

R$^2$ is a group comprising a curable functional group chosen from a vinyl, an acrylate, a methacrylate, a hydroxyl, an alkoxy, an alkenyloxy or an epoxy. R$^2$ may be chosen from a monovalent C1-C20 hydrocarbon radical comprising a curable functional group, a monovalent C4-C20 branched hydrocarbon radical comprising a curable functional group, or a monovalent C4 to C30 cyclic hydrocarbon radical comprising a curable functional group. The $R^2$ group may be represented, in embodiments, by the formula: $X-R^{16}-$ where X is the curable functional group, and $R^{16}$ is a bond or a monovalent hydrocarbon radical. In embodiments, $R^{16}$ may be a C1-C20 alkylene group; a C1-C10 alkylene group; even a C1-C6 alkylene group. X may be chosen from a vinyl group ($CH_2=CH_2-$), an unsaturated cyclic group, an unsaturated polycyclic group, etc. In embodiments, X is chosen from cyclopenetene, cyclohexene, cyclooctene, pinene, bornene, norpinene, norbornene, spiro[2.2]pentene, spiro[2.3]hexene, spiro[2.4]heptene, spiro[2.5]octene, spiro[3.3]heptene, spiro[3.4]octene, spiro[3.5]nonene, spiro[4.4]nonene, spiro[4.5]decene, spiro[5.5]undecene, bicyclo In embodiments, the polymer comprises an aromatic group attached to one of the silicon atoms, e.g., $R^3$-$R^{14}$. In embodiments, the $R^5$ and $R^{11}$ groups in the polymer comprise an aromatic group. In embodiments, the aromatic group is a phenyl group. While not being bound to any particular theory, the presence of aryl groups may be desirable to limit the mobility of the silicon atoms.

In embodiments, the organopolysiloxane (a) comprises polycyclic groups and aromatic groups. The polycyclic groups may be in the siloxane chain (e.g., $R^1$) and at the terminal position (i.e., $R^2$). In embodiments, the $R^5$ and groups in the polymer comprise an aromatic group. In one embodiment, the organopolysiloxane (a) is a compound of the formula:

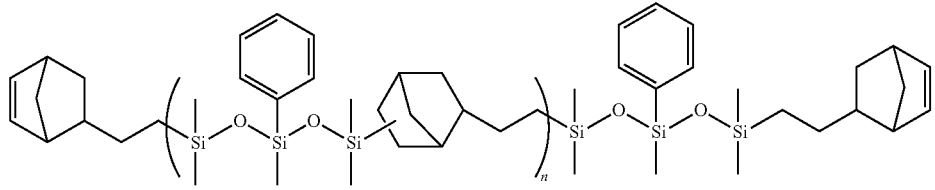

[1.1.0]butene, bicyclo[2.1.0]pentene, bicyclo[2.2.0]hexene, bicyclo[3.1.0]hexene, bicyclo[3.2.0]heptene, bicyclo[3.3.0]octene, bicyclo[4.1.0]heptene, bicyclo[4.2.0]octene, bicyclo[4.3.0]nonene, bicyclo[4.4.0]decene, bicyclo[1.1.1]pentene, bicyclo[2.1.1]hexene, bicyclo[2.2.1]heptene, bicyclo[2.2.2]octene, bicyclo[3.1.1]heptene, bicyclo[3.2.1]octene, bicyclo[3.2.2]nonene, bicyclo[3.3.1]nonene, bicyclo[3.3.2]decene, bicyclo[3.3.3]undecene, an adamantane, tricyclo[5.2.1.0$^{2,6}$] decene, tricyclo[4.3.1.1$^{2,5}$]undecene rings, a limonene, a camphene, a limonene oxide, a vinyl cyclohexyl epoxide, a dicyclopentadiene, 5-ethylidene-2-norbornene, 2-vinyl adamantane, 2-methylene adamantane, (−)-beta-chamigrene, 4-vinyl cyclohexyl, and the like.

Examples of suitable $R^2$ or X groups include, but are not limited to:

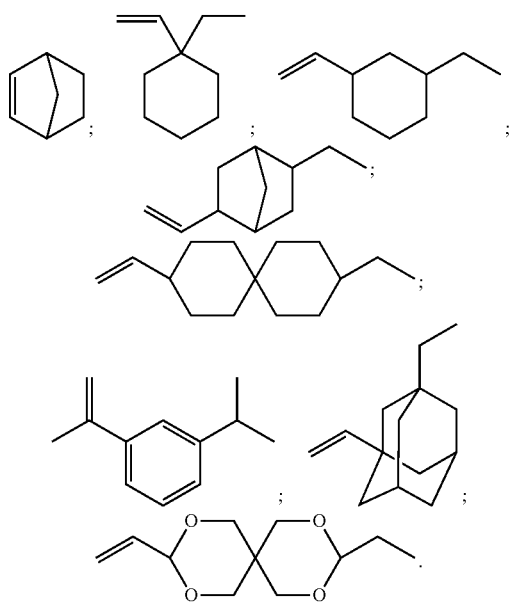

The cross-linker (b) comprises a functional group that is reactive with the curable functional group of the organopolysiloxane (a). In embodiments, the cross-linker (b) comprises a Si—H group, an S—H group, or a combination of two or more thereof. In embodiments, the cross-linker is chosen from a linear silicone, a branched silicone, or a cyclic silicone material comprising a Si—H or S—H group. It will be appreciated that combinations of different cross-linker compounds may be used as desired.

In embodiments, the cross-linker (b) is chosen from a silyl hydride. The silyl hydride is not particularly limited. In embodiments, the silyl hydride may be chosen from a compound of the formula $R^{17}_g SiH_{4-g}$, $(R^{17}O)_g SiH_{4-g}$, $HSiR^{17}_g(OR^{17})_{3-g}$, $R^{17}_3 Si(CH_2)_f(SiR^{17}_2 O)_k SiR^{17}_2 H$, $(R^{17}O)_3 Si(CH_2)_f(SiR^{17}_2 O)_k SiR^{17}_2 H$, $Q_u T_v T^H_p D_r D^H_s M^H_r M_e$, $R^{17}_3 Si(CH_2)_h SiOSiR^{17}_2 (OSiR^{17}_2)_j OSiR^{17}_2 H$, or combinations of two or more thereof. Each occurrence of $R^{17}$ is independently a C1-C18 alkyl, a C1-C18 substituted alkyl, wherein $R^{17}$ optionally contains at least one heteroatom, each occurrence of g independently has a value from 0 to 3, f has a value of 1 to 8, k has a value of 0 to 3000, each of p, u, v, r and e independently has a value from 0 to 20, t and s are from 0 to 3000, provided that p+s+r equals 1 to 1000 and the valences of the all the elements in the silyl hydride are satisfied. As used herein, M represents a monofunctional group of formula $R^{18}_3 SiO_{1/2}$, D represents a difunctional group of formula $R^{18}_2 SiO_{2/2}$, T represents a trifunctional group of formula $R^{18} SiO_{3/2}$, Q represents a tetrafunctional group of formula $SiO_{4/2}$, an $M^H$ represents $HR^{18}_2 SiO_{1/2}$, $T^H$ represents $HSiO_{3/2}$, and $D^H$ represents $R^{18} HSiO_{2/2}$; each occurrence of $R^{18}$ is independently C1-C18 alkyl, C1-C18 substituted alkyl, wherein $R^{18}$ optionally contains at least one heteroatom; h is 1-8, and j is 0-10.

Some non-limiting examples of silyl hydrides include methylhydrogensiloxydimethylsiloxane copolymers, include those from Gelest such as, e.g., HMS 501 HPM-502, HMS-992, HMS-064, polyhydrosilsesquioxane, and other hydride-containing copolymers or homopolymers of dimethyl siloxane or phenyl-containing siloxanes. Other suitable silyl hydrides include those present in SYLGARD 184 (a two-part silicone available from Dow Corning, Midland, Mich.) that was supplied free from the thermohydrosilation catalyst that the commercial version usually contains.

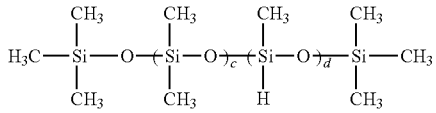

HMS-501-Methylhydrogensilovydimethylsiloxane copolymer

The following structure shows one example of an organo-hydrogenpolysiloxane (HDP-111-hydride terminated polyphenyl(dimethylhydrosiloxy)siloxane, available from Gelest Inc., Tullytown, Pa.) having phenyl functionality.

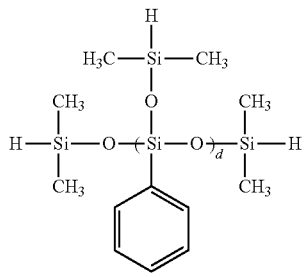

HDP-111-Hydride-terminated
polyphenyl (dimethylhydrogensiloxy)siloxane

Other examples of silyl hydride agents include a Q resin, which may also be referred to as HQ-type resins or hydride-modified silica Q resins. Examples of those compounds include, but are not limited to, those commercially available under the tradename MQH-9™ (Clariant LSM, Inc.), which is a hydride-modified silica Q resin characterized by a molecular weight of 900 g/mole and an activity of 9.5 equivalents/kg; HQM 105™ (Gelest, Inc.), which is a hydride modified silica Q resin characterized by a molecular weight of 500 g/mole and an activity of 8-9 equivalents/kg; and HQM 107™ (Gelest, Inc), which is a hydride-modified silica Q resin characterized by a molecular weight of 900 g/mole and an activity of 8-9 equivalents/kg.

Examples of suitable mercapto-functional siloxanes include, but are not limited to, products such as KF-2001 and KF-2004 by Shin-Etsu Chemical Co., Ltd., SMS-022, SMS-042 and SMS-992 by Gelest Inc.; PS848, PS849, PS849.5, PS850, PS850.5 and PS927 by United Chemical Corp.; and B 7610 available from Momentive Performance Materials Inc.

The cross-linker (b) may also be chosen from a compound of the formula:

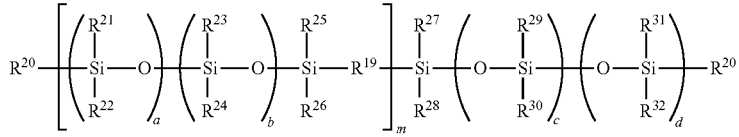

where $R^{19}$ is a divalent organic group chosen from a C1-C20 divalent hydrocarbon, a C4-C20 branched divalent hydrocarbon, or a C4-C30 cyclic-containing divalent hydrocarbon group;

$R^{20}$ is a functional group chosen from hydrogen, an acrylate, a methacrylate, a thiol, or $R^2$;

$R^{21}$-$R^{32}$ are independently chosen from hydrogen, a C1-C10 monovalent hydrocarbon group, a $C^6$-$C^{20}$ monovalent aromatic group, and a C4 to C30 monovalent cycloalkyl group;

a and d are independently 1-30;

b and c are independently 0-30; and m is 1-30.

$R^{19}$ may be chosen from any group suitable as the $R^1$ group described above, and $R^{21}$-$R^{32}$ may be chosen from any group suitable as $R^3$-$R^{14}$ described above. For the sake of brevity, however, the details of those groups are not repeated.

The composition includes a reaction accelerator (c) to effect curing of the organopolysiloxane (a) and the cross-linker (b). The reaction accelerator (c) may be, for example, a photoinitiator, a thermal initiator, a metal catalyst, or a combination of two or more thereof.

In embodiments, the reaction accelerator comprises a catalyst, e.g., a hydrosilation catalyst. Useful catalysts include those compounds or molecules that can catalyze the hydrosilation reaction between a reactive SiH-containing moiety or substituent and a carbon-carbon bond such as a carbon-carbon double bond. Also, in one or more embodiments, these catalysts may be soluble within the reaction medium. Types of catalysts include transition metal compounds including those compounds that include a Group VIII metal. Exemplary Group VIII metals include palladium, rhodium, germanium, and platinum. Exemplary catalyst compounds include chloroplatinic acid, elemental platinum, chloroplatinic acid hexahydrate, complexes of chloroplatinic acid with sym-divinyltetramethyldisiloxane, dichloro-bis(triphenylphosphine) platinum (II), cis-dichloro-bis(acetonitrile) platinum (II), dicarbonyldichloro-platinum (II), platinum chloride, and platinum oxide, zero valent platinum metal complexes such as Karstedt's catalyst, [Cp*Ru(MeCN)3]PF6, [PtCl2(cyclooctadiene)], solid platinum supported on a carrier (such as alumina, silica or carbon black), platinum-vinylsiloxane complexes (e.g., $Pt_n$(ViMe$_2$SiOSiMe$_2$Vi)$_n$ and Pt[(MeViSiO)$_4$]$_m$)), platinum-phosphine complexes (e.g., Pt(PPh$_3$)$_4$ and Pt(PBU$_3$)$_4$)), and platinum-phosphite complexes (e.g., Pt[P(Oph)$_3$]$_4$ and Pt[P(Obu)$_3$]$_4$)), wherein Me represents methyl, Bu represents butyl, "Vi" represents vinyl and Ph represents phenyl, and n and m represent integers. Others include RhCl(PPh$_3$)$_3$, RhCl$_3$, Rh/Al$_2$O$_3$, RuCl$_3$, IrCl$_3$, FeCl$_3$, AlCl$_3$, PdCl$_2$.2H$_2$O, NiCl$_2$, TiCl$_4$, etc.

In embodiments, a photoinitiator may be employed as the reaction accelerator to promote curing of the siloxanes. The photoinitiator can be chosen as desired for a particular purpose or intended application. Examples of suitable photoinitiators include, but are not limited to, benzophenones, phosphine oxides, nitroso compounds, acryl halides, hydrazones, mercapto compounds, pyrillium compounds, triacrylimidazoles, benzimidazoles, chloroalkyl triazines, benzoin ethers, benzil ketals, thioxanthones, camphorquinone, acyl phosphines, and acetophenone derivatives.

In one embodiment, the photoinitiator is chosen from an acylphosphine. The acyl phosphine can be a mono- or bis-acylphoshine. Examples of suitable acylphosphine oxides include those described in U.S. Pat. No. 6,803,392, which is incorporated herein by reference. Specific examples of suitable acylphosphine photoinitiators include, but are not limited to, diphenyl(2,4,6-trimethylbenzoyl) phosphine oxide (DAROCUR® TPO), diphenyl(2,4,6-trimethylbenzoyl)phosphine oxide (ESACURE® TPO, LAMBERTI Chemical Specialties, Gallarate, Italy), diphenyl(2,4,6-trimethylbenzoyl)phosphine oxide (FIRSTCURE® HMPP available from Albemarle Corporation, Baton Rouge, La.), diphenyl(2,4,6-trimethylbenzoyl)phosphine oxide (LUCIRIN® TPO, available from BASF (Ludwigshafen, Germany), diphenyl(2,4,6-trimethylbenzoyl)phosphinate (LUCIRIN® TPO-L), phenyl bis(2,4,6-trimethyl benzoyl) phosphine oxide (IRGACURE® 819, available from Ciba Specialty Chemicals, Tarrytown, N.Y.), and bis(2,6-dimethoxybenzoyl)-2,4,4-trimethylpentylphosphine oxide (as IRGACURE® 1700, IRGACURE® 1800 and IRGACURE® 1850 in admixture with a-hydroxyketones from Ciba Spezialitatenchemie).

Examples of α-hydroxyketone photoinitiators can include 1-hydroxy-cyclohexylphenyl ketone (IRGACURE® 184), 2-hydroxy-2-methyl-1-phenyl-1-propanone (DAROCUR® 1173), and 2-hydroxy-1-[4-(2-hydroxyethoxy)phenyl]-2-methyl-1-propanone (IRGACURE® 2959), all available from Ciba Specialty Chemicals (Tarrytown, N.Y.).

Examples of α-aminoketones photoinitiators can include 2-benzyl-2-(dimethylamino)-1-[4-(4-morpholinyl)phenyl]-1-butanone (IRGACURE® 369), and 2-methyl-1-[4-(methylthio)phenyl]-2-(4-morpholinyl)-1-propanone (IRGACURE® 907), both available from Ciba Specialty Chemicals (Tarrytown, N.Y.).

The curable composition may optionally comprise a polymerization inhibitor (d). The polymerization inhibitor is not particularly limited and may be chosen as desired for a particular purpose or intended use. Inhibitors for component (d) of the platinum group metal catalysts are well known in the organosilicon art. Examples of suitable inhibitors include, but are not limited to, ethylenically unsaturated amides, aromatically unsaturated amides, acetylenic compounds, ethylenically unsaturated isocyanates, olefinic siloxanes, unsaturated hydrocarbon diesters, unsaturated hydrocarbon mono-esters of unsaturated acids, conjugated or isolated enzymes, hydroperoxides, ketones, sulfoxides, amine, phosphines, phosphites, nitrites, diaziridines, etc. Particularly suitable inhibitors for the compositions are alkynyl alcohols and maleates. Examples of suitable polymerization inhibitors include, but are not limited to, diallyl maleate, hydroquinone, p-methoxyphenol, t-butylcatechol, phenothiazine, etc.

The amount of component (d) to be used in the compositions is not critical and can be any amount that will retard the above described platinum catalyzed hydrosilylation reaction at room temperature while not preventing said reaction at moderately elevated temperature, i.e. a temperature that is 25 to 125° C. above room temperature. No specific amount of inhibitor can be suggested to obtain a specified bath life at room temperature since the desired amount of any particular inhibitor to be used will depend upon the concentration and type of the platinum metal containing catalyst, the nature and amounts of components a and b. The range of component (d) can be 0 to about 10% weight, about 0.001 wt to 2% by weight, even about 0.12 to about 1 by weight. Here as elsewhere in the specification and claims, numerical values can be combined to form new and alternative ranges. In one embodiment, the compositions can be free of any inhibitor component (d).

The curable composition may also comprise other additives (e). Other additives may include, but are not limited to, an adhesion promoter, an antioxidant, a filler, pigments, dyes, filler treating agent, plasticizer, spacer, extender, biocide, stabilizer, flame retardant, surface modifier, anti-aging additive, rheological additive, corrosion inhibitor, surfactant or combination thereof.

Various organofunctional silane and siloxane adhesion promoters to inorganic substrates are useful in the composition. Suitable silanes include, but are not limited to, amino silanes, epoxy silanes, isocyanurate silanes, mercapto silanes, imido silanes, anhydride silanes, carboxylate functionalized siloxanes, etc. Combinations of various types of adhesions promoters may also be used. Such components typically hinder curing via metal catalyzed hydrosilylation. Suitable adhesion promoters include, but are not limited to various aminosilane materials such as Silquest® A-1120 silane, Silquest A-1110 silane, Silquest A-2120 silane, and Silquest A-1170 silane; epoxysilanes, such as Silquest A-187 silane; isocyanurate silanes such as Silquest A-597 silane; and mercaptosilanes such as Silquest A-189 silane, Silquest A-1891 silane, Silquest A-599 silane available from Momentive Performance Materials.

The curable compositions may also include an antioxidant compound. Examples of suitable classes of antioxidant compounds include, but are not limited to, hindered amines and/or hindered phenol compounds.

Examples of hindered amine antioxidant compounds include, but are not limited to Hindered amine series antioxidant (N,N',N'',N'''-tetrakis-(4,6-bis(butyl-(N-methy)-2,2,6,6-tetramethylpiperidin-4-yl)amino)-triazine-2-yl)-4,7-diazadecan-1,10-diamine, a polycondensation product of dibutylamine-1,3,5-triazine-N,N'-bis-(2,2,6,6-tetramethyl-4-piperidyl-1,6-hexamethylenediamine-N-(2,2,6,6-tetramethyl-4-piperidyl)butylamine, poly[{6-(1,1,3,3-tetramethylbutyl)amino-1,3,5-triazine-2,4-diyl}{(2,2,6,6-tetramethyl-4-piperidyl)imino}hexamethylene{(2,2,6,6-tetramethyl-4-piperidyl)imino}], a polymer of dimethyl succinate and 4-hydroxy-2,2,6,6-tetramethyl-1-piperidinethanol, [a reaction product of decanedioic acid bis(2,2,6,6-tetramethyl-1 (octyloxy)-4-piperidyl) ester, 1,1-dimethylethylhydroperoxide and octane] (70%)-polypropylene (30%), bis(1,2,2,6,6-pentamethyl-4-piperidyl)[[3,5-bis(1,1-dimethylethyl)-4-hydroxyphenyl]methyl]butylmalonate, methyl 1,2,2,6,6-pentamethyl-4-piperidylsebacate, bis(2,2,6,6-tetramethyl-4-piperidyl)sebacate, bis(1,2,2,6,6-pentamethyl-4-piperidyl) sebacate, 1-[2-[3-(3,5-di-tert-butyl-4-hydroxyphenyl) propionyloxy]ethyl]-4-[3-(3,5-di-tert-butyl-4-hydroxyphenyl)propionyloxy]-2,2,6,6-tetramethylpiperidine, 4-benzoyloxy-2,2,6,6-tetramethylpiperidine, 8-acetyl-3-dodecyl-7,7,9,9-tetramethyl-1,3,8-triazaspiro[4.5]decan-2,4-dione, etc.)

In one embodiment, the antioxidant compound is a hindered phenolic compound. The hindered phenol can be chosen as desired for a particular purpose or intended application. Examples of suitable hindered phenols include, but are not limited to, monophenols such as 2,6-di-t-butyl-p-cresol, 2-t-butyl-4-methoxyphenol, 3-t-butyl-4-methoxyphenol, and 2,6-t-butyl-4-ethylphenol, bisphenols such as 2,2'-methylene-bis(4-methyl-6-t-butylphenol), 4,4'-thiobis (3-methyl-6-t-butylphenol), and 4,4'-butylidene-bis(3-methyl-6-t-butylphenol); and polymeric phenols such as 1,1,3-tris(2-methyl-4-hydroxy-5-t-butylphenyl)butane, 1,3, 5-trimethyl-2,4,6-tris(3,5-di-t-butyl-4-hydroxybenzyl)benzene, tetrakis[methylene-3-(3',5'-di-t-butyl-4'-hydroxyphenyl)propionate]methane, bis[3,3'-bis(4'-hydroxy-3-t-butylphenyl)butyric acid glycol ester, and tocopherol (vitamin E), pentaerythritol-tetrakis[3-(3,5-di-tert-butyl-4-hydroxyphenyl)propionate], thiodiethylene-bis[3-(3,5-di-tert-butyl-4-hydroxyphenyl)propionate], octadecyl-3-(3,5-di-tert-butyl-4-hydroxyphenyl)propionate), N,N'-hexane-1,6-diylbis[3-(3,5-di-tert-butyl-4-hydroxyphenylpropioamide), benzenepropanoic acid 3,5-bis (1,1-dimethylethyl)-4-hydroxy C7-C9 side chain alkyl ester, 2,4-dimethyl-6-(1-methylpentadecyl)phenol, diethyl[[3,5-bis(1,1-dimethylethyl)-4-hydroxyphenyl]methyl]phosphonate, 3,3',3'',5,5',5''-hexane-tert-butyl-4-a,a',a''-(mesitylene-2,4,6-tolyl)tri-p-cresol, calcium diethylbis[[[3,5-bis-(1,1-dimethylethyl)-4-hydroxyphenyl]methyl]phosphonate], 4,6-bis(octylthiomethyl)-o-cresol, ethylenebis(oxyethylene)bis [3-(5-tert-butyl-4-hydroxy-m-tolyl)propionate], hexamethylenebis[3-(3,5-di-tert-butyl-4-hydroxyphenyl) propionate], 1,3,5-tris(3,5-di-tert-butyl-4-hydroxybenzyl)-1,3,5-triazine-2,4,6-(1H,3H,5H)-trione, a reaction product of N-phenylbenzeneamine and 2,4,4-trimethylpentene, 2,6-di-tert-butyl-4-(4,6-bis(octylthio)-1,3,5-triazine-2-ylamino) phenol etc.).

IRGANOX 1330 is a sterically hindered phenolic antioxidant ("3,3',3',5,5',5'-hexa-tert-butyl-a,a',a'-(mesitylene-2,4,6-triyl)tri-p-cresol") commercially available from BASF. Irganox 1010 is a sterically hindered phenolic antioxidant ("Pentaerythritol Tetrakis(3-(3,5-di-tert-butyl-4-hydroxyphenyl)propionate)") commercially available from BASF, or 1,3,5-trimethyl-2,4,6-tris(3,5-di-tert-butyl-4-hydroxybenzyl) benzene commercially available as ETHANOX™ 330 (Albemarle Corporation), pentaerythritol tetrakis[3-(3,5-di-tert-butyl-4-hydroxyphenyl)propionate] (Irganox 1010), tris (3,5-di-tert-butyl-4-hydroxybenzyl) isocyanurate (Irganox 3114), tris(3,5-di-tert-butyl-4-hydroxybenzyl) isocyanurate as Irganox 3114.

The curable composition may optionally comprise a photostabilizer. The photostabilizer is not particularly limited and may be chosen as desired for a particular application or intended use. Examples of suitable materials for the photostabilizer include, bur are not limited to, 2,4-di-tert-butyl-6-(5-chlorobenzotriazol-2-yl)phenol, 2-(2H-benzotriazol-2-yl)-4,6-di-tert-pentylphenol, 2-(2H-benzotriazol-2-yl)-4-(1,1,3,3-tetramethylbutyl)phenol, a reaction product of methyl 3-(3-(21-1-benzotriazol-2-yl)-5-tert-butyl-4-hydroxyphenyl)propionate/polyethylene glycol 300, 2-(2H-benzotriazol-2-yl)-6-(straight and branched dodecyl)-4-methylphenol, 2-(4,6-diphenyl-1,3,5-triazine-2-yl)-5-[(hexyl)oxy]-phenol, octabenzone, 2,4-di-tert-butylphenyl-3,5-di-tert-butyl-4-hydroxybenzoate, tinuvin 622LD, Tinuvin 144, CHIMASSORB 119FL, MARK LA-57, LA-62, LA-67, LA-63, SANDOL LS-765, LS-292, LS-2626, LS-1114, LS-744, etc.

The curable composition may comprise the organopolysiloxane (a) in an amount of from about 5 to about 98 mass %; from about 10 to about 90 mass %; or about 20 to about 80 mass %. The cross-linker (b) may be present in an amount of from about 2 to about 25 mass %; from about 6 to about 20%; or about 6 to about 12 mass %. The reaction accelerator (c) may be present in an amount of from about 0.0001 to about 0.2 mass %; from about 0.0002 to about 0.05 mass %; or about 0.0005 to about 0.02 mass %. The inhibitor (d) may be present in an amount of from about 0.0001 to about 1 mass %; from about 0.0002 to about 0.6 mass %; or about 0.0005 to about 0.3 mass %. Adhesion promoters may be present in an amount of from about 0.1 to about 10 mass %; from about 0.3 to about 5 mass %; or about 0.5 to about 3 mass %.

The curable composition may have a refractive index of greater than about 1.45, 1.5, 1.55, or 1.6. In embodiments, the curable composition has a refractive index of from about 1.45 to about 1.6, or from about 1.5 to about 1.55.

The curable composition may also exhibit excellent optical clarity. In embodiments, the curable composition has a transparency of about 95% or greater, about 96% or greater, about 97% or greater, about 98% or greater, even about 99% or greater at 400 nm to about 800 nm.

Curing the curable organosilicon composition of the present invention yields a cured product that has a high degree of hardness and excellent transparency, crack resistance and heat resistance. There are no particular restrictions on the curing conditions, which vary depending on the quantity of the composition, but the curing temperature is preferably within a range from 60 to 180° C., and the curing time is typically within a range from 0.5 to 10 hours. In embodiments, curing can be achieved in 30 minutes at a temperature of about 100° C.

The cured material formed from the curable composition may also exhibit desirable properties for a variety of applications. In embodiments, curable composition may have a refractive index of greater than about 1.45. In embodiments, the curable composition has a refractive index of from about 1.45 to about 1.5.

The cured material may also exhibit excellent optical clarity. In embodiments, a 1 mm thick sheet of the cured material has a transparency of about 95% or greater, about 96% or greater, about 97% or greater, about 98% or greater, even about 99% or greater at 400 nm to about 800 nm.

The cured material may also exhibit high thermal stability and crack resistance.

The cured material may also exhibit good moisture vapor permeability. In embodiments, a 1 mm thick sheet of the cured material has a moisture vapor permeability of from about 10 to about 15 g/m$^2$ day under the JISZ0208 test method.

The curable organosilicon composition of the present invention is useful as a curable silicone material, an encapsulating material for optical devices such as optical elements, an encapsulating material for other electronic devices such as semiconductor elements, and an electrically insulating coating material. Examples of optical devices include optical elements such as LEDs, semiconductor lasers, photodiodes, phototransistors, solar cells and CCDs; and optical components such as lenses, bonding materials, adhesives, films, sheets, etc. The cured material may be used as an encapsulant, e.g., an LED encapsulant. Examples of electronic devices include semiconductor elements such as diodes, transistors, ICs, CPUs and memory elements.

The curable silicone compositions can be included in a personal care composition such as, but not limited to, cosmetics, sunscreen, hair products such as shampoo or conditioner, lotions, creams, etc. Personal care compositions can include various ingredients such as a carrier, pigment, film formers, emulsifiers, vitamins, plasticizers, surfactants, antioxidants, waxes, oils, solvents, etc.

In one embodiment, a personal care product may optionally contain 0-90 parts by weight pigments. Pigments suitable for use herein are all inorganic and organic colors/pigments. These are usually aluminum, barium or calcium salts or lakes. Lakes are either a pigment that is extended or reduced with a solid diluent or an organic pigment that is prepared by the precipitation of a water-soluble dye on an adsorptive surface, which usually is aluminum hydrate. A lake also forms from precipitation of an insoluble salt from an acid or basic dye. Calcium and barium lakes are also used herein. Suitable lakes include, but are not limited to, Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake. Other colors and pigments can also be included in the compositions, such as pearls, titanium oxides, Red 6, Red 21, Blue 1, Orange 5, and Green 5 dyes, chalk, talc, iron oxides and titanated micas.

A personal care composition may optionally contain 0-99 parts by weight organic film former known in the prior arts. The film-forming agent may be any which is cosmetically acceptable. Examples of useful film-forming agents include natural waxes, polymers such as polyethylene polymers, and copolymers of PVP, ethylene vinyl acetate, dimethicone gum, and resins, such as shellac, polyterpenes.

A personal care composition may optionally include 0-50 parts by weight either blocking or absorbing sunscreening agents. Blocking sunscreening agents are generally inorganic, such as various cesium oxides, chromium oxides, cobalt oxides, iron oxides, red petrolatum, silicone- and other treated titanium dioxides, titanium dioxide, zinc oxide, and/or zirconium oxide, $BaTiO_3$, $CaTiO_3$, $SrTiO_3$ and SiC. Absorbing sunscreening agents, which are usually organic species, are particularly useful. Such absorbing sunscreening agents include, but are not limited to, UV-A absorbers, which generally absorb radiation in the 320 to 400 nm region of the ultraviolet spectrum, for example anthranilates, benzophenones, and dibenzoyl methanes; and UV-B absorbers, which generally absorb radiation in the 280 to 320 nm region of the ultraviolet spectrum, for example, p-aminobenzoic acid derivatives, camphor derivatives, cinnamates, and salicylates. Specific examples of organic sunscreening agents include p-aminobenzoic acid, avobenzone cinoxate, dioxybenzone, homosalate, menthyl anthranilate, octocrylene, octyl methoxycinnamate, octyl salicylate, oxybenzone, padimate, phenylbenzimidazole sulfonic acids, sulisobenzone, trolamine salicylate, aminobenzoic acid, amyldimethyl p-aminobenzoic acid, diethanolamine p-methoxycinnamate, digalloyl trioleate, 2-ethylhexyl-2-cyano-3,3-diphenylacrylate, ethylhexylp-methoxycinnamate, 2-ethylhexyl salicylate, glyceryl aminobenzoate, homomenthyl salicylate, homosalate, 3-imidazol-4-ylacrylic acid and the ethyl ester thereof, methyl anthranilate, octyldimethyl PABA, 2-phenylbenzimidazole-5-sulfonic acid and salts, sulisobenzone, triethanolamine salicylate, N,N,N-trimethyl-4-(2-oxoborn-3-ylidene methyl)anillinium methyl sulfate, aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammonium)-benzyliden-boman-2-one methyl sulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, ca-(2-oxoborn-3-ylidene)-tolyl-4-sulfonic acid and soluble salts thereof, 3-(4'-sulfo) benzyliden-bornan-2-one and soluble salts thereof, 3-(4'-methylbenzylidene)-d,l-camphor, 3-benzylidene-d,l-camphor, benzene 1,4-di(3-methylidene-10-camphosulfonic) acid and salts thereof, urocanic acid, 2,4,6-tris-(2'-ethylhexyl-1'-oxycarbonyl)-anilinol 1,3,5-triazine, 2-(p-(tert-butylamido)anilinol-4,6-bis-(p-(2'-ethylhexyl oxycarbonyl) anilinol 1,3,5-triazine, 2,4-bis{1,4-(2-ethylhexyloxy)-2-hydroxyl-phenyl}-6-(4-methoxyphenyl)-1,3,5-triazine, the polymer of N-(2 et 4)-(2-oxoborn-3-yliden) methylbenzyl acrylamide, 1,4-bisbenzimidazolyl-phenylen-3,3',5,5'-tetrasulfonic acid and salts thereof, the benzalmalonate-substituted polyorganosiloxanes, the benzotriazole-substituted polyorganosiloxanes (Drometrizole Trisiloxane), solubilized 2,2'-methylene-bis-1,6-(2H-benzotriazol-2-yl)-4-(1,1,3,3-tetramethylbutyl) phenol, 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, and combinations comprising at least one of the foregoing sunscreening agents.

A personal care composition can be specifically formulated for use as, but not limited to, a color cosmetic, sunscreen, hair conditioner, a moisturizer, etc. Suitable forms and formulations for such application are known to those of ordinary skill in the art. For example, when formulated for use as a sunscreen, the composition may be in the form of a lamellar emulsion, a mirocoemulsion, or a nanoemulsion. In addition, the emulsions may be a fluid simple emulsion, a fluid multiple emulsion, a rigid simple emulsion, or a rigid multiple emulsion. The simple emulsion or multiple emulsion may comprise a continuous aqueous phase containing dispersed lipid vesicles or oil droplets, or a continuous fatty phase dispersed lipid vesicles or water droplets. In one embodiment, the sunscreen application is an emulsion having a continuous aqueous phase, and may be in the form of a stick, a lotion, a gel, a spray, and the like. Suitable emulsifiers for the formation of sunscreen emulsions include, for example ethoxylated surfactants known in the art such as Polysorbate-20, Laureth-7, Laureth-4, Sepigel® 305 available from SEPPIC, oils such as vegetable and mineral oil; animal and/or synthetic waxes such as beeswax, paraffin, rice bran wax, candelilla wax, carnauba wax and derivatives thereof; and hydrocarbon gels or bentone type gels, such as Gel SS71, Gel EA2786, Quaternium-18 Bentonite, 38 CE, Gel ISD V or Gel ISD; and organosilicone emulsifiers such as cetyl dimethicone copolyol-polyglyceryl4-isostearate-hexylaurate (ABIL® WE 09) available from Goldschmidt Chemical Corporation, behenate dimethicone, cetyl dimethicone copolyol (ABIL® EM 90), (ABIL® EM 97), laurylmethicone copolyol (5200), cyclomethicone and dimethicone copolyol (DC 5225 C and DC 3225 C), cyclopentasiloxane and dimethicone copolyol (SF 1528).

A personal care composition may optionally contain vitamins or skin nourishing agents. Some suitable agents are ceramides, hyaluronic Acid, panthenol, peptides (copper hexapeptide-3), AHA's (lactic acid), retinols (retinyl palmitate)- Vit. A derivatives, vitamin C (l-ascorbic acid), BHA's (salicylic Acid), teas (Green Tea, White Tea, Red Tea), soy and other plant derivatives, isoflavones (Grape Seed Extract), argireline, acai berry.

Plasticizers may also be added to the formulation to improve the flexibility and cosmetic properties of the resulting formulation. Plasticizers are frequently used to avoid brittleness and cracking of film formers, and include, for example, lecithin, polysorbates, dimethicone copolyol, glycols, citrate esters, glycerin, and dimethicone. One skilled in the art may routinely vary the amount of plasticizer desired based on the properties desired and the application envisaged.

The composition of the present invention can be incorporated into a carrier, such as a volatile carrier which quickly volatilizes after application. The volatile carriers can be selected from volatile hydrocarbons, volatile silicones, and mixtures thereof.

Hydrocarbon oils useful in personal care products include those having boiling points in the range of 60-260° C., including hydrocarbon oils having from about $C_8$ to about $C_{20}$ chain lengths, even $C_8$ to $C_{20}$ isoparaffins. Examples include isododecane, isohexadecane, isoeocosane, 2,2,4-trimethylpentane, 2,3-dimethylhexane, and mixtures of two or more thereof.

Suitable volatile silicone fluids include cyclomethicones having 3, 4 and 5 membered ring structures corresponding to the formula $(R_2SiO)_x$, where x is from about 3 to about 6.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

EXAMPLES

Aspects of this disclosure will now be described and may be further understood with respect to the following examples. The examples are intended to be illustrative only and are to be understood as not limiting the invention disclosed herein in any way as to materials, or process parameters, equipment or conditions.

Examples 1: Preparation of Component (A-1)

A norbornene end-capped phenylmethyl silicone norbornenylethyl block copolymer (A-1) having molecular weight 3 kD was synthesized according to the following scheme:

A 500 mL three neck round bottom flask fitted with a reflux condenser, dropping funnel and a mechanical stirrer under nitrogen environment was charged 100 mL of toluene and 5-vinylbicyclo[2.2.1]hept-2-ene (128.7 g, 1.07 mol). To this solution 0.289 g of Karstedt's catalyst (15 ppm of 2 wt % Pt) was added. The whole set-up was kept in an oil bath with the reaction temperature maintained at 50° C. 3-phenyl-1,1,3,3,5-pentatmethyltrisiloxane (257.51 g, 0.95 mol) in a dropping funnel was added drop wise over a period of 1 h. The reaction temperature was subsequently increased to 80° C. and allowed to continue until all the hydride of gets consumed. After completion of the hydrosilylation polymerization, unreacted starting materials, volatile compounds and the solvent were stripped under reduced pressure. The final product was obtained as a yellow color liquid in quantitative yield and was decolorized with activated charcoal to yield the desired product as a colorless liquid in quantitative yield (Viscosity at 25° C.: 6810 mPa·s; GPC: $M_n$=3.06 kD; $M_w$=4.6 kD; PDI=1.5)

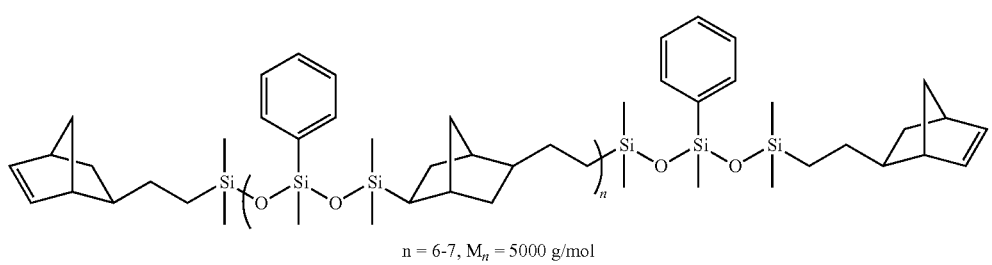

A1 n = 6-7, $M_n$ = 5000 g/mol

Example 2: Preparation of Component (A-2)

A norbornene end-capped phenylmethyl silicone norbornenylethyl block copolymer (component A-2) having molecular weight of 140 kD was synthesized similar to the method described for A-1.

Briefly, in to a 500 mL three neck round bottom flask 150 mL of toluene and 5-vinylbicyclo[2.2.1]hept-2-ene (94 g, 0.78 mol). To this solution 0.225 g of Karstedt's catalyst (15 ppm of 2 wt % Pt) was added. 3-phenyl-1,1,3,3,5-pentatmethyltrisiloxane (200 g, 0.74 mol) in a dropping funnel was added drop wise into the reaction mixture at 50° C. over a period of 1 h. The reaction temperature was subsequently increased to 80° C. and allowed to continue until all the hydride of gets consumed. After completion of the hydrosilylation polymerization, unreacted starting materials, volatile compounds and the solvent were stripped under reduced pressure. The final product was obtained as a yellow color liquid in quantitative yield and was decolorized with activated charcoal to yield the desired product as a colorless liquid in quantitative yield. (Viscosity at 25° C.: 14200 mPa·s; GPC: $M_n$=5.2 kD; $M_w$=7.8 kD; PDI=1.5)

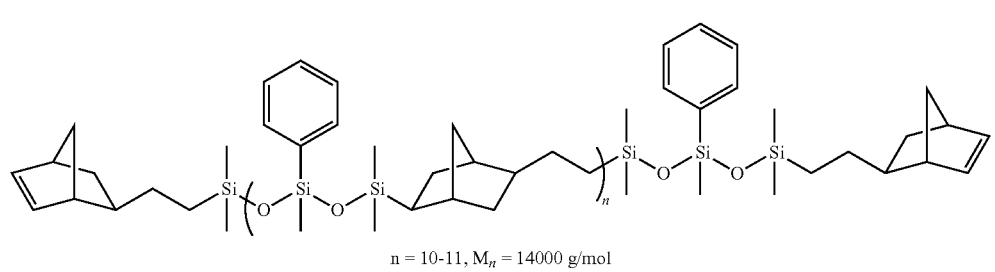

A1 n = 10-11, $M_n$ = 14000 g/mol

Example 3: Preparation of Component (B-1)

A hydride end-capped phenylmethyl silicone norbornenylethyl block copolymer (component B) was synthesized according to the following scheme:

A 500 mL three neck round bottom flask fitted with a reflux condenser, dropping funnel and a mechanical stirrer under nitrogen environment was charged 100 mL of toluene and 5-vinylbicyclo[2.2.1]hept-2-ene (200 g, 1.66 mol). To this solution 0.529 g of Karstedt's catalyst (15 ppm of 2 wt % Pt) was added. The whole set-up was kept in an oil bath with reaction temperature maintained at 50° C. 3-phenyl-1,1,3,3,5-pentatmethyltrisiloxane (506.47 g, 1.87 mol) in a dropping funnel was added drop wise over a period of 1 h. The reaction temperature was subsequently increased to 80° C. and continue the reaction until all the 5-vinylbicyclo [2.2.1]hept-2-ene gets consumed. After completion of the hydrosilylation polymerization, unreacted starting materials, volatile compounds and the solvent were stripped under reduced pressure. The final product was obtained as a yellow color liquid in quantitative yield and was decolorized with activated charcoal to yield the desired product as a colorless liquid in quantitative yield. The chemical structure and composition of the copolymers are inferred through spectral, chromatographic and thermal analysis.

to generate a thickness of 1 mm, and was then heated at 130° C. for 1 hours, thus yielding a cured product.

B-2

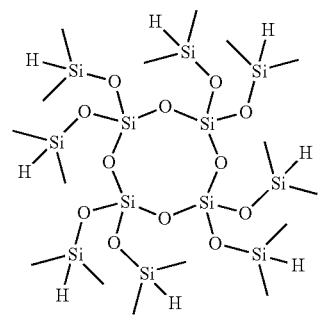

B-3

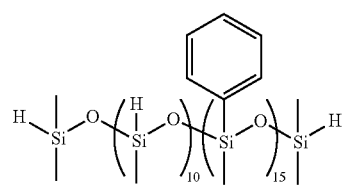

B1

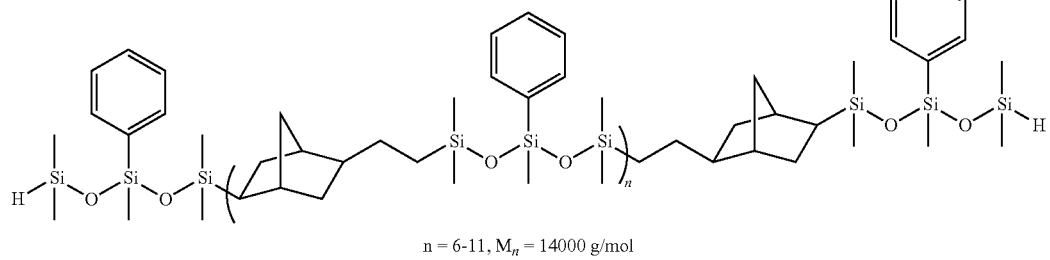

n = 6-11, $M_n$ = 14000 g/mol

Example 4

A curable silicone composition was prepared by mixing 87.7 parts by mass of the copolymer obtained in the Example 1 (referred as A-1 hereafter), 0.025 parts by mass of a platinum-vinylsiloxane complex (platinum concentration: 1.8% by 1,3,5,7-tetravinylmethylcyclosiloxane oil solution) as a curing catalyst, 0.125 parts by mass of diallyl maleate as reaction inhibitor. Subsequently, to the resulting mixture was added 12.15 parts by mass of a component B-2 (referred as cross linking agent 1). The composition was mixed thoroughly in a speed mixer until a homogeneous distribution of the components is achieved. This composition was then poured into a mold formed from glass plates

Example 5

A curable silicone composition was prepared by mixing 85.5 parts by mass of the copolymer obtained in the Example 1 (A-1), 0.025 parts by mass of a platinum-vinylsiloxane complex (platinum concentration: 1.8% by 1,3,5,7-tetravinylmethylcyclosiloxane oil solution) as a curing catalyst and 0.125 parts by mass of diallyl maleate as reaction inhibitor. Subsequently, to the resulting mixture was added 14.35 parts by mass of a component B-3 as cross linking agent. The entire composition was mixed thoroughly in a speed mixer until a homogeneous distribution of the components is achieved. This composition was then poured into a mold formed from glass plates to generate a thickness of 1 mm, and was then heated at 130° C. for 1 hour, thus yielding a cured product.

Example 6

A curable silicone composition was prepared by mixing 86.6 parts by mass of the copolymer obtained in the Example 1 (A-1), 0.025 parts by mass of a platinum-vinylsiloxane complex (platinum concentration: 1.8% by 1,3,5,7-tetravinylmethylcyclosiloxane oil solution) as a curing catalyst and 0.125 parts by mass of diallyl maleate as reaction inhibitor. Subsequently, to the resulting mixture were added 6.075 parts by mass of a component B-2 and 7.175 parts by mass of a component B-3 as cross linking agents. The entire composition was mixed thoroughly in a speed mixer until a homogeneous distribution of the components is achieved. This composition was then poured into a mold formed from glass plates to generate a thickness of 1 mm, and was then heated at 130° C. for 1 hour, thus yielding a cured product.

Example 7

A curable composition was prepared in the same manner as mentioned in the Example 6, except that diallyl maleate was replaced by 0.125 parts by mass of 3,5-dimethylhex-1-yn-3-ol as reaction inhibitor. The composition was cured at 130° C. for 1 hour following procedures stated in the previous examples.

Example 8

A curable silicone composition was prepared by mixing 91.1 parts by mass of the copolymer obtained in the Example 2 (A-2), 0.025 parts by mass of a platinum-vinylsiloxane complex (platinum concentration: 1.8% by 1,3,5,7-tetravinylmethylcyclosiloxane oil solution) as a curing catalyst and 0.125 parts by mass of diallyl maleate as reaction inhibitor. Subsequently, to the resulting mixture was added 8.75 parts by mass of a component B-2 as cross linking agent. The entire composition was mixed thoroughly in a speed mixer until a homogeneous distribution of the components is achieved. This composition was then poured into a mold formed from glass plates to generate a thickness of 1 mm, and was then heated at 130° C. for 1 hour yielding a cured product.

Example 9

A curable composition was prepared similar to the composition mentioned in Example 7 with the addition of 0.1 parts by mass of 1,3,5-tris[4-hydroxy-3,5-bis(2-methyl-2-propanyl)benzyl]-1,3,5-triazinane-2,4,6-trione (manufactured by BASF, trade name: Irganox 3114) additionally to the composition. A 1 mm cured sheet was obtained by curing the composition at 130° C. for 1 hour into a mold formed from glass plates following procedure mentioned previously.

Example 10: Cure Composition with the Thiol X-Linker

A curable silicone composition was prepared by including 95 parts of the silicone composition of Example 1, 4.5 parts of a thiol cross-linker and 0.5 parts of a photoinitiator (Darcour 1173) of the formula MDDS$^H$M (SMS-992 available from Gelest, Inc.) by exposing the composition to UV radiation at a dose of 4500 mJ/cm$^2$. The resulting cured product was observed highly transparent.

Performance Evaluation

Properties of the cured sheet obtained from the examples were evaluated (1 mm) by the following methods. The results have been summarized in Table 1.

Viscosity of the curable composition was measured at 25° C. using HAAKE RheoStress 600.

To obtain information about the external appearance, the cured sheet of each example was inspected visually.

Transparency of the cured sheet was measured by spectrophotometer (Gretag Macbeth Color Eye 7000A spectrophotometer).

The water vapor permeability (WVTR) of the cured articles was evaluated using permeability cup tester from Yasuda Seiki Seisakusho, Ltd. by following method JIS Z 0208.

The cured products obtained from the examples were colorless and transparent and also exhibited a high degree of flexibility. Furthermore, they also exhibited resistance to coloration on exposure to heat & light, indicating their applicability in optoelectronic application as encapsulant and barrier adhesives.

TABLE 1

| Properties | Ex-4 | Ex-5 | Ex-6 | Ex-7 | Ex-8 | Ex-9 |
| --- | --- | --- | --- | --- | --- | --- |
| Appearance | Transparent & colorless | Transparent & colorless | Transparent & colorless | Transparent & colorless | Transparent & colorless | Transparent & colorless |
| Viscosity [Pas] (uncured) | 2.16 | 4.30 | 3.10 | 3.13 | — | — |
| Transmittance (%) (cured) | >98% | >98% | >98% | >98% | >98% | >98% |
| Hardness (TYPE A) (cured) | 54 | 48 | 51 | 53 | — | — |
| WVTR (g/m$^2$ · day) (cured@900 μm) | 9.8 | 10.9 | 10.4 | 10.6 | 10.7 | 11.2 |

The foregoing description identifies various non-limiting embodiments of a heater assembly. Modifications may occur to those skilled in the art and to those who may make and use the invention. The disclosed embodiments are merely for illustrative purposes and not intended to limit the scope of the invention or the subject matter set forth in the claims.

What is claimed is:

1. A curable silicone composition comprising:
(A) an organopolysiloxane with a formula:

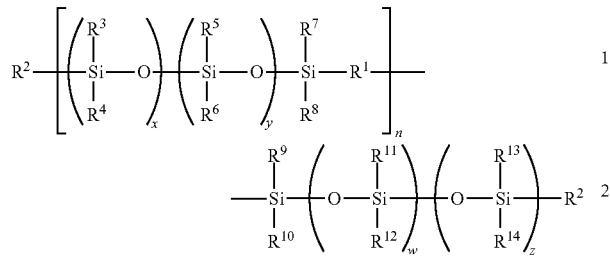

where $R^1$ is chosen from a divalent group comprising a C4-C30 cyclic-containing hydrocarbon group chosen from a cyclobutyl group, cyclopentyl group, a cyclohexyl group, a cycloheptyl group, a cyclooctyl group, 1,1-diethenyl cylcohexane; 1,3-diethenyl cylcohexane; bicyclo[2.2.1]-2,5-dienthenylheptane; 1,4-di-2-prope-1-nylcyclochexane; 1,3-diisopropenylbenzene; a spiro[5.5]-3,8-diethenylundecane; a 1,3-diethenyladamantane; a vinyl norbornene; 3,9-divinyl-2,4,8,10-tetraoxaspiro[5.5]undecane; pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5]undecane, bicyclo[1.1.0]butane, bicyclo[2.1.0]pentane, bicyclo[2.2.0]hexane, bicyclo[3.1.0]hexane, bicyclo[3.2.0]heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.2.2]nonane, bicyclo[3.3.1]nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings;
$R^2$ is a curable functional group independently chosen from a vinyl, a vinyl-containing group, an unsaturated hydrocarbon, an unsaturated cyclic hydrocarbon, an acrylate, a methacrylate, a hydroxy, an alkoxy, and an epoxy;
$R^3$-$R^{14}$ are independently chosen from hydrogen, a C1-C10 monovalent hydrocarbon group, a C6-C20 monovalent aromatic group, and a C4 to C30 monovalent saturated or unsaturated cycloalkyl group;
x and z are independently 1-30;
y and w are independently 0-30; and
n is 1-30;
(B) a cross-linker selected from a compound of the formula:

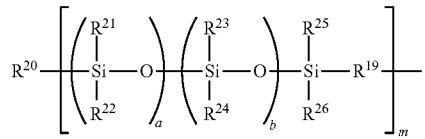

-continued

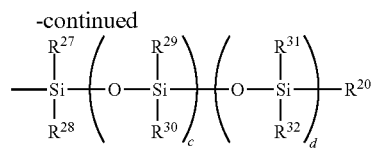

where $R^{19}$ is a divalent organic group chosen from a C1-C20 divalent hydrocarbon, a C4-C20 branched divalent hydrocarbon, or a C4-C30 cyclic-containing divalent hydrocarbon group;
$R^{20}$ is a functional group chosen from hydrogen, an acrylate, a methacrylate, a thiol, or $R^2$;
$R^{21}$-$R^{32}$ are independently chosen from hydrogen, a C1-C10 monovalent hydrocarbon group, a $C^6$-$C^{20}$ monovalent aromatic group, and a C4 to C30 monovalent cycloalkyl group;
a and d are independently 1-30;
b and c are independently 0-30; and
m is 1-30;
(C) a reaction accelerating agent selected from a photoinitiator, a thermal initiator, a metal containing catalyst, or a combination of two or more thereof;
(D) optionally an inhibitor; and
(E) optionally one or more additives.

2. The curable silicone composition of claim 1, wherein $R^2$ is chosen from a C1-C20 hydrocarbon radical comprising a vinyl functional group, a monovalent C4-C20 branched hydrocarbon radical comprising a vinyl functional group, or a monovalent C4 to C30 cyclic hydrocarbon radical comprising a vinyl functional group.

3. The curable silicone composition of claim 1, wherein $R^2$ is of the formula X—$R^{16}$— where X is the curable functional group chosen from a vinyl group ($CH_2$=$CH_2$—), an unsaturated cyclic group, an unsaturated polycyclic group, and $R^{16}$ is a bond or a monovalent hydrocarbon.

4. The curable silicone composition of claim 3, wherein X is chosen from cyclopentene, cyclohexene, cyclooctene, pinene, bornene, norpinene, norbornene, spiro[2.2]pentene, spiro[2.3]hexene, spiro[2.4]heptene, spiro[2.5]octene, spiro[3.3]heptene, spiro[3.4]octene, spiro[3.5]nonene, spiro[4.4]nonene, spiro[4.5]decene, spiro[5.5]undecene, bicyclo[1.1.0]butene, bicyclo[2.1.0]pentene, bicyclo[2.2.0]hexene, bicyclo[3.1.0]hexene, bicyclo[3.2.0]heptene, bicyclo[3.3.0]octene, bicyclo[4.1.0]heptene, bicyclo[4.2.0]octene, bicyclo[4.3.0]nonene, bicyclo[4.4.0]decene, bicyclo[1.1.1]pentene, bicyclo[2.1.1]hexene, bicyclo[2.2.1]heptene, bicyclo[2.2.2]octene, bicyclo[3.1.1]heptene, bicyclo[3.2.1]octene, bicyclo[3.2.2]nonene, bicyclo[3.3.1]nonene, bicyclo[3.3.2]decene, bicyclo[3.3.3]undecene, an adamantene, tricyclo[5.2.1.0$^{2,6}$]decene, tricyclo[4.3.1.1$^{2,5}$]undecene rings, a limonene, a camphene, a limonene oxide, a vinyl cyclohexyl epoxide, a dicyclopentadiene, 5-ethylidene-2-norbornene, 2-vinyl adamantane, 2-methylene adamantane, or (−)-beta-chamigrene, 4-vinyl cyclohexyl.

5. The curable silicone composition of claim 1, further comprising an additional cross-linker chosen from a silicone-containing compound comprising at least one —SiH group, at least one —SH group, or a combination of two or more thereof.

6. The curable silicone composition of claim 5, wherein the silicone-containing compound of the additional cross-linker is chosen from a cyclic silicone, a linear silicone, a branched silicone, or a combination of two or more thereof.

7. The curable silicone composition of claim 1, wherein $R^{19}$ is chosen from a divalent organic group comprising a C4-C30 cyclic-containing hydrocarbon group chosen from a cyclopentyl group, a cyclohexyl group, a cycloheptyl group, cyclooctyl group, bicyclo[2.2.1]hepta-2,5-diene; a 1,1-diethenyl cylcohexane; a 1,3-diethenyl cylcohexane; a bicyclo[2.2.1]-2,5-dienthenylheptane; a 1,4-di-2-prope-1-nylcyclochexane; a 1,3-diisopropenylbenzene; a spiro[5.5]-3,8-diethenylundecane; a 1,3-diethenyladamantane; a vinyl norbornene; 3,9-divinyl-2,4,8,10-tetraoxaspiro[5.5]undecane; pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5]undecane, bicyclo[1.1.0]butane, bicyclo[2.1.0]pentane, bicyclo[2.2.0]hexane, bicyclo[3.1.0]hexane, bicyclo[3.2.0]heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.2.2]nonane, bicyclo[3.3.1]nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings.

8. The curable silicone composition of claim 1, wherein the reaction accelerating agent is selected from a metal-containing catalyst.

9. The curable silicone composition of claim 1, wherein the inhibitor is selected from an ethylenic compound, an acetylenic compound, or a combination thereof.

10. The curable silicone composition of claim 1, wherein the additive is selected from an antioxidant, a thermal stabilizer, an adhesion promoter, a filler, or a combination of two or more thereof.

11. The curable silicone composition of claim 1, wherein the composition has a refractive index of from 1.45 to 1.51.

12. The curable silicone composition of claim 1, wherein the composition has a transparency of ≥95%.

13. The curable silicone composition of claim 1, wherein the composition has a moisture vapor transmission rate of about 10 to about 15 g/m²·day, O permeability of 10$^{-1}$ to 10 g/m²·day.

14. A personal care composition comprising the curable silicone composition of claim 1.

15. The personal care composition of claim 14, wherein the personal care composition is chosen from a cosmetic formulation, a sunscreen, a shampoo, a conditioner, a lotion, or a cream.

16. A cured article formed from a curable silicone composition, said curable silicone composition comprising:

(A) an organopolysiloxane with a general formula:

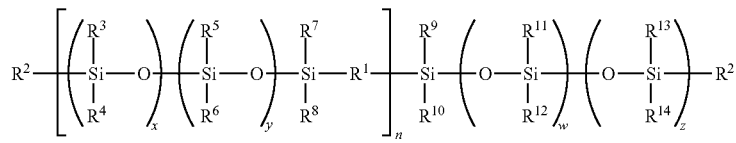

where R$^1$ is chosen from a divalent organic group comprising a C4-C30 cyclic-containing hydrocarbon group chosen from a cyclobutyl group, cyclopentyl group, a cyclohexyl group, a cycloheptyl group, cyclooctyl group, 1,1-diethenyl cylcohexane; 1,3-diethenyl cylcohexane; bicyclo[2.2.1]-2,5-dienthenylheptane; 1,4-di-2-prope-1-nylcyclochexane; 1,3-diisopropylbenzene; spiro[5.5]-3,8-diethenylundecane; a 1,3-diethenyladamantane; a vinyl norbornene; 3,9-divinyl-2,4,8,10-tetraoxaspiro[5.5]undecane; pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5]undecane, bicyclo[1.1.0]butane, bicyclo[2.1.0]pentane, bicyclo[2.2.0]hexane, bicyclo[3.1.0]hexane, bicyclo[3.2.0]heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.2.2]nonane, bicyclo[3.3.1]nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings;

R$^2$ is a curable functional group independently chosen from a vinyl, a vinyl-containing group, an unsaturated hydrocarbon, an unsaturated cyclic hydrocarbon, an acrylate, a methacrylate, a hydroxy, an alkoxy, and an epoxy;

R$^3$-R$^{14}$ are independently chosen from hydrogen, a C1-C10 monovalent hydrocarbon group, a C6-C20 monovalent aromatic group, and a C4 to C30 monovalent saturated or unsaturated cycloalkyl group;

x and z are independently 1-30;

y and w are independently 0-30; and n is 1-30;

(B) a cross-linker is selected from a compound of the formula:

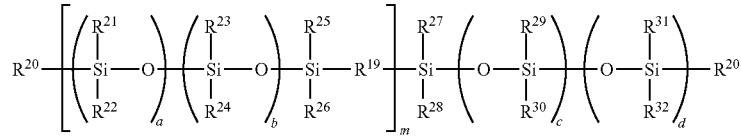

where R$^{19}$ is a divalent organic group chosen from a C1-C20 divalent hydrocarbon, a C4-C20 branched divalent hydrocarbon, or a C4-C30 cyclic-containing divalent hydrocarbon group;

R$^{20}$ is a functional group chosen from hydrogen, an acrylate, a methacrylate, a thiol, or R$^2$;

R$^{21}$-R$^{32}$ are independently chosen from hydrogen, a C1-C10 monovalent hydrocarbon group, a C$^6$-C$^{20}$ monovalent aromatic group, and a C4 to C30 monovalent cycloalkyl group;

a and d are independently 1-30;

b and c are independently 0-30; and m is 1-30;

(C) a reaction accelerating agent is selected from a photoinitiator, a thermal initiator and a metal containing catalyst;

(D) optionally an inhibitor;

(E) optionally one or more additives.

17. The cured article of claim 16, wherein the $R^2$ functional group chosen from a C1-C20 hydrocarbon radical comprising a vinyl functional group, a monovalent C4-C20 branched hydrocarbon radical comprising a vinyl functional group, or a monovalent C4 to C30 cyclic hydrocarbon radical comprising a vinyl functional group.

18. The cured article of claim 16, wherein the $R^2$ group is of the formula X—$R^{16}$— where X is the curable functional group, and $R^{16}$ is a bond or a monovalent hydrocarbon radical.

19. The cured article of claim 18, wherein $R^{16}$ is a C1-C20 alkylene group, and X is chosen from a vinyl group ($CH_2$=$CH_2$—), an unsaturated cyclic group, or an unsaturated polycyclic group.

20. The cured article of claim 18, wherein X is chosen from cyclopentene, cyclohexene, cyclooctene, pinene, bornene, norpinene, norbornene, spiro[2.2]pentene, spiro[2.3]hexene, spiro[2.4]heptene, spiro[2.5]octene, spiro[3.3]heptene, spiro[3.4]octene, spiro[3.5]nonene, spiro[4.4]nonene, spiro[4.5]decene, spiro[5.5]undecene, bicyclo[1.1.0]butene, bicyclo[2.1.0]pentene, bicyclo[2.2.0]hexene, bicyclo[3.1.0]hexene, bicyclo[3.2.0]heptene, bicyclo[3.3.0]octene, bicyclo[4.1.0]heptene, bicyclo[4.2.0]octene, bicyclo[4.3.0]nonene, bicyclo[4.4.0]decene, bicyclo[1.1.1]pentene, bicyclo[2.1.1]hexene, bicyclo[2.2.1]heptene, bicyclo[2.2.2]octene, bicyclo[3.1.1]heptene, bicyclo[3.2.1]octene, bicyclo[3.2.2]nonene, bicyclo[3.3.1]nonene, bicyclo[3.3.2]decene, bicyclo[3.3.3]undecene, an adamantene, tricyclo[5.2.1.0$^{2,6}$]decene, tricyclo[4.3.1.1$^{2,5}$]undecene rings, a limonene, a camphene, a limonene oxide, a vinyl cyclohexyl epoxide, a dicyclopentadiene, 5-ethylidene-2-norbornene, 2-vinyl adamantane, 2-methylene adamantane, (−)-beta-chamigrene, 4-vinyl cyclohexyl.

21. The cured article of claim 16, further comprising an additional cross-linker chosen from chosen from a silicone-containing compound comprising at least one —SiH group, at least on —SH group, or a combination of two or more thereof.

22. The cured article of claim 21, wherein the silicone-containing compound of the additional cross-linker is chosen from a cyclic silicone, a linear silicone, a branched silicone, or a combination of two or more thereof.

23. The cured article of claim 16, wherein $R^{19}$ is chosen from a divalent organic group comprising a C4-C30 cyclic-containing group chosen from a cyclopentyl group, a cyclohexyl group, a cycloheptyl group, cyclooctyl group, 1,1-diethenyl cylcohexane; a 1,3-diethenyl cylcohexane; bicyclo[2.2.1]-2,5-dienthenylheptane; 1,4-di-2-prope-1-nylcyclochexane; 1,3-diisopropenylbenzene; spiro[5.5]-3,8-diethenylundecane; 1,3-diethenyladamantane; 3,9-divinyl-2,4,8,10-tetraoxaspiro[5.5]undecane; pinane, bornane, norpinane, norbornane, spiro[2.2]pentane, spiro[2.3]hexane, spiro[2.4]heptane, spiro[2.5]octane, spiro[3.3]heptane, spiro[3.4]octane, spiro[3.5]nonane, spiro[4.4]nonane, spiro[4.5]decane, spiro[5.5]undecane, bicyclo[1.1.0]butane, bicyclo[2.1.0]pentane, bicyclo[2.2.0]hexane, bicyclo[3.1.0]hexane, bicyclo[3.2.0]heptane, bicyclo[3.3.0]octane, bicyclo[4.1.0]heptane, bicyclo[4.2.0]octane, bicyclo[4.3.0]nonane, bicyclo[4.4.0]decane, bicyclo[1.1.1]pentane, bicyclo[2.1.1]hexane, bicyclo[2.2.1]heptane, bicyclo[2.2.2]octane, bicyclo[3.1.1]heptane, bicyclo[3.2.1]octane, bicyclo[3.2.2]nonane, bicyclo[3.3.1]nonane, bicyclo[3.3.2]decane, bicyclo[3.3.3]undecane, an adamantyl, tricyclo[5.2.1.0$^{2,6}$]decane tricyclo[4.3.1.1$^{2,5}$]undecane rings.

24. The cured article of claim 16, wherein the reaction accelerating agent is selected from a metal containing catalyst.

25. The cured article of claim 16, wherein the inhibitor is selected from a ethylenic compounds or a acetylenic compounds or a combination thereof.

26. The cured article of claim 16, wherein the additive is selected from an antioxidant, a thermal stabilizer, an adhesion promoter, filler, or a combination thereof.

27. The cured article of claim 16, wherein the article has a refractive index of from 1.45 to 1.51.

28. The cured article of claim 16, wherein the article has a transparency of ≥95%.

29. The cured article claimed in claim 16, wherein the article has a moisture vapor transmission rate of about 10 to about 15 g/m$^2$·day, O permeability of $10^{-1}$ to 10 g/m$^2$·day.

30. The cured article of claim 16, wherein the article is chosen from an LED encapsulant, an optical waveguide, an optical lens, an optical bonding material, an optical adhesive, an a optical film or sheet, laminated film of sheet, in electronic component or in combination with semiconductor device.

* * * * *